(12) United States Patent
Hoshino et al.

(10) Patent No.: US 7,351,716 B2
(45) Date of Patent: *Apr. 1, 2008

(54) DERMATOLOGICAL PREPARATIONS

(75) Inventors: Masahide Hoshino, Tochigi (JP); Yoshiya Sugai, Tochigi (JP); Akiyo Kameyama, Tochigi (JP); Hiroaki Saito, Tochigi (JP); Yoshinori Nishizawa, Tochigi (JP); Yutaka Takagi, Tochigi (JP)

(73) Assignee: Kao Corporation, Tokyo (JP)

( * ) Notice: Subject to any disclaimer, the term of this patent is extended or adjusted under 35 U.S.C. 154(b) by 665 days.

This patent is subject to a terminal disclaimer.

(21) Appl. No.: 10/731,249

(22) Filed: Dec. 10, 2003

(65) Prior Publication Data

US 2004/0115162 A1 Jun. 17, 2004

Related U.S. Application Data

(62) Division of application No. 09/926,270, filed as application No. PCT/JP00/01383 on Mar. 8, 2000, now Pat. No. 6,685,953.

(30) Foreign Application Priority Data

Apr. 8, 1999 (JP) ................... 11-101076

(51) Int. Cl.
*A61K 7/48* (2006.01)
*A61K 7/00* (2006.01)
*A61K 7/06* (2006.01)
*C07C 233/18* (2006.01)

(52) U.S. Cl. .................................... 514/310
(58) Field of Classification Search ................ 424/401; 514/310
See application file for complete search history.

(56) References Cited

U.S. PATENT DOCUMENTS

| 3,773,056 | A | 11/1973 | Kalopissis et al. |
|---|---|---|---|
| 4,778,823 | A | 10/1988 | Kawamata et al. |
| 4,985,547 | A | 1/1991 | Yano et al. |
| 5,028,416 | A | 7/1991 | Yano et al. |
| 5,071,971 | A | 12/1991 | Yano et al. |
| 5,175,321 | A | 12/1992 | Ohashi et al. |
| 5,446,027 | A | 8/1995 | Fujimori et al. |
| 5,659,052 | A | 8/1997 | Ohashi et al. |
| 5,753,707 | A | 5/1998 | Hoshino et al. |
| 5,756,784 | A | 5/1998 | Uno et al. |
| 5,801,258 | A | 9/1998 | Ohashi et al. |
| 5,863,945 | A | 1/1999 | Murayama et al. |
| 6,685,953 | B1 * | 2/2004 | Hoshino et al. ............ 424/401 |

FOREIGN PATENT DOCUMENTS

| EP | 0 447 064 A2 | 9/1991 |
|---|---|---|
| JP | 4-128256 | 4/1992 |
| JP | 10-218849 | 8/1998 |

OTHER PUBLICATIONS

Grigoryan et al., Synthesis and Antistaphylococcal Activity of Dicarboxylic Acid Derivatives Containing an Amino Acid Fragment, Khimiko-Farmatsevticheski Zhurnal (1992), 26(2), 43-5, abstract.
JP 10-218849, Kao Corp Machine Assisted Translation of Glyceryl-Etherified Amide Compound and Composition of Agent for External Use Containing the Same, Aug. 18, 1998, Entire Reference.
Ott, Robert J., Research Disclosure (1976) 152, 24-5.

* cited by examiner

*Primary Examiner*—Ardin Marschel
*Assistant Examiner*—Zohreh Vakili
(74) *Attorney, Agent, or Firm*—Oblon, Spivak, McClelland, Maier & Neustadt, P.C.

(57) ABSTRACT

The present invention relates to a dermatologic preparation containing a diamide derivative represented by the following formula (1):

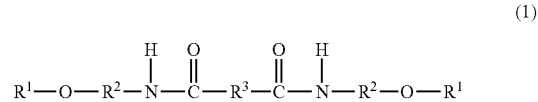

(wherein, $R^1$ represents a linear or branched hydrocarbon group having 1 to 22 carbon atoms which may be substituted by one or more hydroxy and/or alkoxy groups, $R^2$ represents a linear or branched divalent hydrocarbon group having 1 to 12 carbon atoms, and $R^3$ represents a linear or branched divalent hydrocarbon group having 1 to 42 carbon atoms). This diamide derivative (1) is capable of fundamentally improving the water retention capacity and barrier functions of the horny layer, is excellent in miscibility and mixing stability and can be prepared efficiently at a low cost.

8 Claims, No Drawings

DERMATOLOGICAL PREPARATIONS

TECHNICAL FIELD

The present invention relates to dermatologic preparations capable of exerting excellent effects of maintaining normal barrier functions of the horny layer, restoring and reinforcing damaged barrier functions, heightening water retention of the horny layer and remedying skin chapping; and novel diamide derivatives having such effects.

BACKGROUND ART

When the water retention capacity or barrier functions of the horny layer are weakened by some internal or external reasons, the skin suffers from troubles such as chapping and acceleration of aging. It is therefore highly important to maintain and reinforce the water retention capacity and barrier functions of the horny layer for our healthy daily life.

The present applicant has formerly proposed dermatologic preparations comprising an amide derivative represented by the following formula (3):

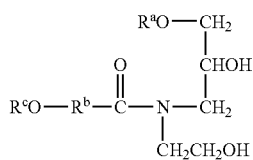

(wherein, $R^a$ represents a linear or branched, saturated or unsaturated hydrocarbon group having 10 to 40 carbon atoms, $R^b$ represents a linear or branched divalent hydrocarbon group having 3 to 39 carbon atoms, $R^c$ represents a hydrogen atom, a linear or branched, saturated or unsaturated hydrocarbon group having 10 to 40 carbon atoms or an acyl group) as a dermatologic preparation capable of essentially improving (maintaining, reinforcing) the barrier functions of the horny layer (Japanese Patent Application Laid-Open (Kokai) No. 4-128256).

Although these amide derivatives exert the above-described excellent effects, they still involve some problems in miscibility or mixing stability because they do not always have sufficient solubility in bases and solution stability. Moreover, preparation of such amide derivatives requires multi-stage reaction, inevitably causing an increase in their production cost.

An object of the present invention is therefore to provide a compound capable of essentially improving the water retention capacity and barrier functions of the horny layer, having improved miscibility or mixing stability, and being available efficiently at a low cost; and a dermatologic preparation which contains the above-described compound and, by maintaining and reinforcing the water retention capacity and barrier functions of the horny layer, exerts effects of preventing or remedying skin troubles such as chapping, protecting the hair with its penetrated component, improving touch feel of the hair and preventing or remedying chapping of the scalp.

DISCLOSURE OF THE INVENTION

The present invention provides a dermatologic preparation, humectant or skin-barrier-function reinforcing agent, which comprises a diamide derivative represented by the following formula (1):

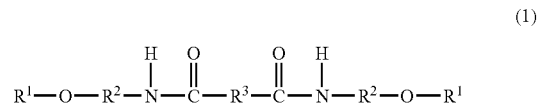

(wherein $R^1$ represents a linear or branched hydrocarbon group having 1 to 22 carbon atoms which may be substituted by one or more hydroxy and/or alkoxy groups, $R^2$ represents a linear or branched divalent hydrocarbon group having 1 to 12 carbon atoms, and $R^3$ represents a linear or branched divalent hydrocarbon group having 1 to 42 carbon atoms).

The present invention also provides a diamide derivative represented by the following formula (2):

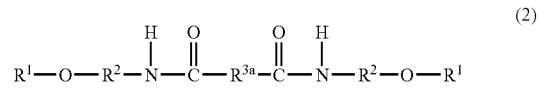

(wherein, $R^1$ represents a linear or branched hydrocarbon group having 1 to 22 carbon atoms which may be substituted by one or more hydroxy and/or alkoxy groups, $R^2$ represents a linear or branched divalent hydrocarbon group having 1 to 12 carbon atoms, and $R^{3a}$ represents an alkylene group or an alkenylene group having 1 to 4 double bonds, which alkylene or alkenylene group may be linear or branched and has 11 to 42 carbon atoms)

BEST MODE FOR CARRYING OUT THE INVENTION

In the diamide derivatives (1) and (2), preferred as $R^1$ are linear or branched $C_{1-22}$ alkyl groups which may have 1 to 3 substituents selected from a hydroxy group and $C_{1-6}$ alkoxy groups. Of these, $C_{1-18}$ alkyl groups, $C_{1-18}$ mono- or di-hydroxyalkyl groups, ($C_{1-6}$ alkoxy-substituted)-($C_{1-18}$ alkyl) groups, and (hydroxy- and $C_{1-6}$ alkoxy-substituted)-($C_{1-18}$ alkyl) groups are preferred, of which $C_{1-18}$ alkyl groups, $C_{2-12}$ mono- or di-hydroxyalkyl groups, ($C_{1-6}$ alkoxy-substituted)-($C_{2-12}$ alkyl) groups, and (hydroxy- and $C_{1-6}$ alkoxy-substituted)-($C_{2-12}$ alkyl) groups are more preferred. Specific examples include methyl, ethyl, propyl, butyl, hexyl, dodecyl, 2-methylpropyl, 2-ethylhexyl, methyl-branched isostearyl, 2-hydroxyethyl, 9-hydroxynonyl, 2,3-dihydroxypropyl, 2-methoxyethyl, 2-hydroxy-3-methoxypropyl and 9-methoxynonyl groups. Of these, 2-hydroxyethyl, methyl, dodecyl and 2-methoxyethyl groups are more preferred.

As $R^2$, linear or branched $C_{1-12}$ alkylene groups are preferred, with linear or branched $C_{2-6}$ alkylene groups being more preferred. Specific examples include ethylene, trimethylene, tetramethylene, pentamethylene, hexamethylene, methylmethylene (ethylidene), 1-methylethylene, 2-methylethylene, 1-methyltrimethylene, 2-methyltrimethylene, 1,1-dimethylethylene and 2-ethyltrimethylene groups, of which ethylene and trimethylene groups are more preferred.

In the formula (1), linear or branched divalent hydrocarbon groups having 2 to 34 carbon atoms are preferred as $R^3$, with alkylene groups and alkenylene groups having 1 to 4 double bonds each of which may be linear or branched and has 2 to 34 carbon atoms, particularly, alkylene groups and alkenylene groups having 1 to 4 double bonds each of which may be linear or branched and has 2 to 24 carbon atoms being preferred. Specific examples include ethylene, trimethylene, tetramethylene, hexamethylene, heptamethylene, octamethylene, decamethylene, undecamethylene, dodecamethylene, tridecamethylene, tetradecamethylene, hexadecamethylene, octadecamethylene, tricosamethylene, hexacosamethylene, triacontamethylene, 1-methylethylene, 2-ethyltrimethylene, 1-methylheptamethylene, 2-methylheptamethylene, 1-butylhexamethylene, 2-methyl-5-ethylheptamethylene, 2,3,6-trimethylheptamethylene, 6-ethyldecamethylene, 7-methyltetradecamethylene, 7-ethylhexadecamethylene, 7,12-dimethyloctadecamethylene, 8,11-dimethyloctadecamethylene, 7,10-dimethyl-7-ethylhexadecamethylene, 1-octadecylethylene, 9,10-dioctyloctadecamethylene, 8,9-dinonylhexadecamethylene, ethenylene, 1-octadecenylethylene, 7,11-octadecadienylene, 7-ethenyl-9-hexadecamethylene, 7,12-dimethyl-7,11-octadecadienylene, 8,11-dimethyl-7,11-octadecadienylene, 9,10-dioctyl-7,11-octadecadienylene and 8,9-dinonyl-6,10-hexadecadienylene groups. Of these, 7,12-dimethyloctadecamethylene, 7,12-dimethyl-7,11-octadecadienylene, octadecamethylene, octamethylene, decamethylene, undecamethylene and tridecamethylene groups are more preferred.

In the formula (2), preferred as $R^{3a}$ are alkylene groups and alkenylene groups having 1 to 4 double bonds each of which may be linear or branched and has 12 to 34 carbon atoms, with alkylene groups and alkenylene groups having 1 to 4 double bonds each of which may be linear or branched and has 12 to 24 carbon atoms being more preferred. Of these, 7,12-dimethyloctadecamethylene, 7,12-dimethyl-7,11-octadecadienylene, octadecamethylene and tridecamethylene groups are still more preferred.

In the diamide derivatives (2) of the present invention, particularly preferred are compounds of the formula (2) having, as $R^1$, $R^2$ and $R^{3a}$, the groups within the above-described more preferred ranges in combination, respectively. In the diamide derivatives (1) to be used for the dermatologic preparations of the present invention, particularly preferred are compounds of the formula (1) having, as $R^1$, $R^2$ and $R^3$, groups within the above-described more preferred ranges in combination, respectively.

Particularly preferred examples of the diamide derivatives (1) to be used for the dermatologic preparations of the present invention include:

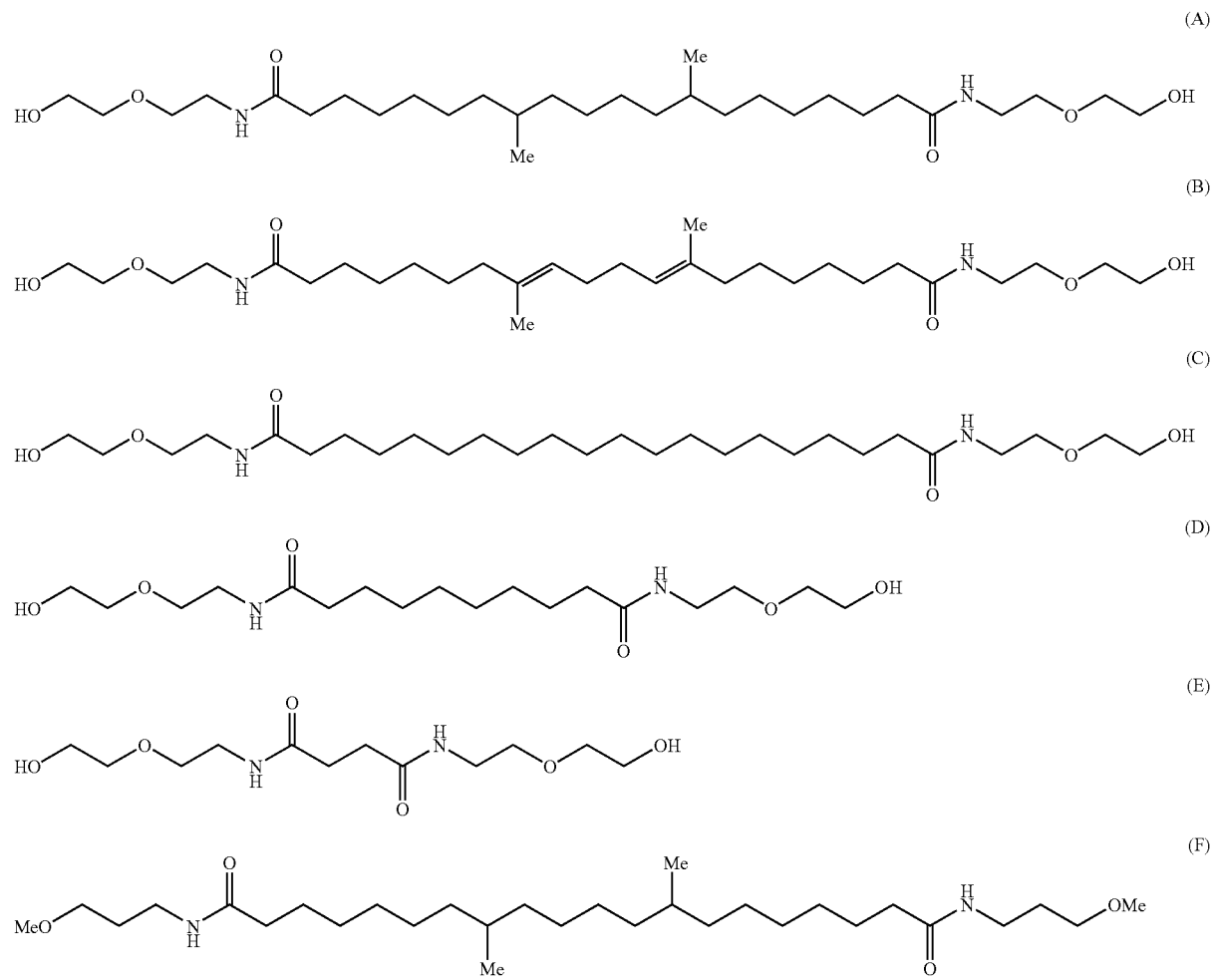

-continued
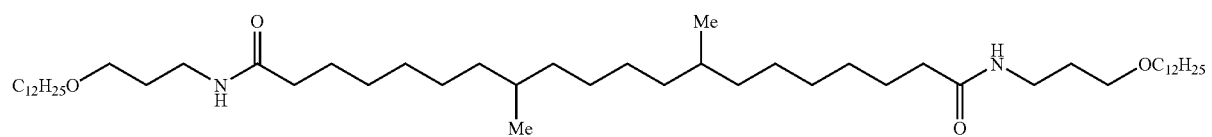
(G)
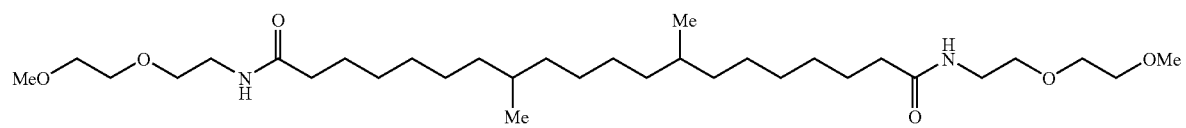
(H)
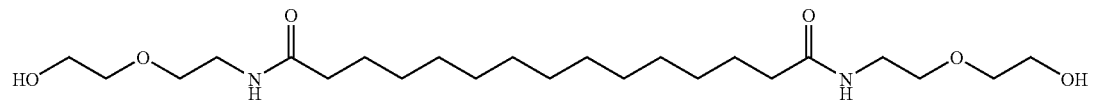
(I)
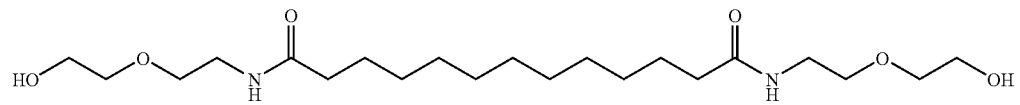
(J)
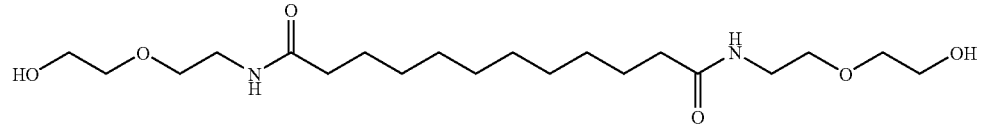
(K)
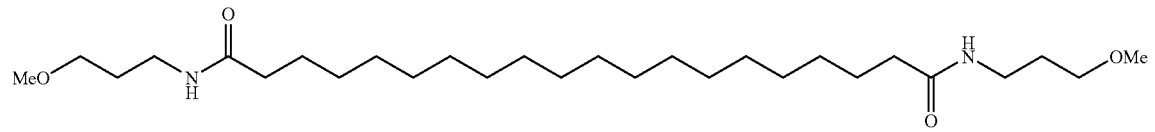
(L)
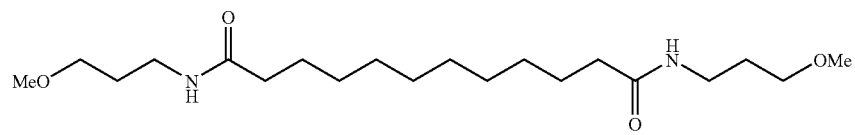
(M)
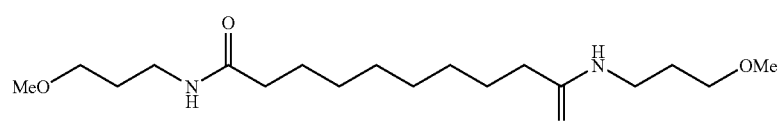
(N)
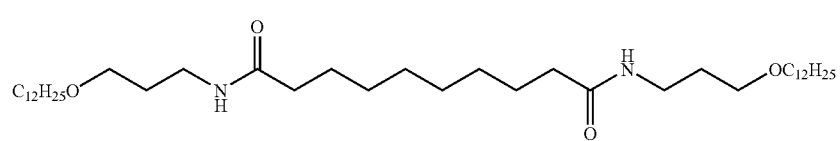
(O)

Particularly preferred examples of the diamide derivatives (2) of the present invention include the above-exemplified compounds (A) to (C), (F) to (J) and (L).

The diamide derivatives (1) to be used for the dermatologic preparations of the present invention can be prepared by a known amide synthesis method. A preparation process, for example, in accordance with the following reaction scheme can efficiently yield them at a low cost.

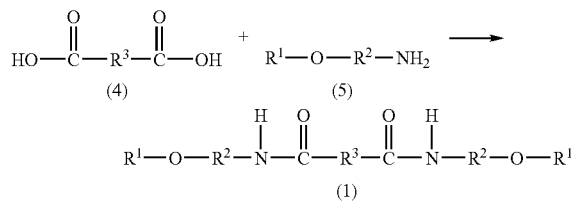

(wherein, $R^1$, $R^2$ and $R^3$ have the same meanings as described above).

The target diamide derivative (1) is available efficiently by condensing a corresponding carboxylic acid (4) or reactive derivative thereof (ester, acid halide or acid anhydride) with an amine (5). This condensation is preferably conducted in the presence or absence of a dehydrating agent such as dicyclohexylcarbodiimide, or a base, for example, an alkali metal hydroxide such as potassium hydroxide or sodium hydroxide, an alkaline earth metal hydroxide such as calcium hydroxide, an alkali metal carbonate such as potassium carbonate, an alkali earth metal carbonate such as calcium carbonate, an alkali metal alcoholate such as sodium methoxide, sodium ethoxide or potassium-tert-butoxide or a tertiary amine such triethylamine or pyridine under a pressure ranging from normal pressure to reduced pressure at 1.3 Pa at room temperature to 250° C. Upon condensation, the amine (5) is preferably used in an excess amount, more specifically, 2 equivalents or greater of the dicarboxylic acid (4) or reactive derivative thereof. For rapid progress of the reaction, it is preferred to conduct the reaction while removing, out of the system, water or an alcohol generated by the reaction. The diamide derivative (1) thus available can be purified in a known manner such as washing with water, column chromatography, distillation, crystallization, recrystallization or powder treatment. Since the diamide derivative (1) obtained in such a manner has effects of penetrating into the lipid layer of the horny layer, thereby maintaining and improving the water retention capacity and barrier functions of the horny layer, it is useful as a humectant or skin-barrier-function reinforcing agent.

The dermatologic preparations of the present invention are obtained by incorporating the amide derivative (1) in a base (carrier) ordinarily employed for dermatologic preparations. They can be prepared by mixing necessary raw materials in a known manner.

The dermatologic preparations of the present invention may be broadly classified into medicinal dermatologic preparations and cosmetics depending on the applications thereof. Examples of the medicinal dermatologic preparations include various ointments containing pharmaceutically effective ingredients. These ointments may contain either an oily base or an O/W or W/O emulsion base. No particular limitation is imposed on the oily base and examples thereof include vegetable oils, animal oils, synthetic oils, fatty acids and natural and synthetic glycerides. No particular limitation is imposed on the pharmaceutically effective ingredients and examples thereof include analgesic antiinflammatory agents, antipruritic agents, bactericides, astringents, skin emollients and hormones as needed.

When the dermatologic preparations of the present invention are used as cosmetics (including skin cosmetics and hair cosmetics), the essential ingredient, that is, the diamide derivative (1), may be arbitrarily blended with commonly used oleaginous components, surfactants, humectants, ultraviolet absorbers, whitening agents, anti-wrinkle compositions, alcohols, chelating agents, pH regulators, antiseptics, thickeners, colorants and perfumes.

These cosmetics may be formulated into various forms such as W/O and O/W emulsion cosmetics, cream, cosmetic milky lotion, cosmetic lotion, oily cosmetic, lipstick, foundation, bath agent, skin cleanser, nail treatment and hair cosmetics. No particular limitation is imposed on the hair cosmetics and examples include hair tonic, hair dressing, hair rinse, hair treatment, hair conditioner, hair styling agent, shampoo, hair nourishment and hair growth stimulant.

Although there is no particular limitation imposed on the content of the diamide derivative (1) in the dermatologic preparation of the present invention. In the case of an emulsion type dermatologic preparation, 0.001 to 50 wt. % (which will hereinafter be described % simply) based on the whole composition is preferred. In the case of an oily dermatologic preparation containing a liquid hydrocarbon such as squalane as a base, 0.01 to 50% based on the whole composition is preferred. In either case, 0.01 to 20% is particularly preferred. Particularly, for prevention or remedy of chapping, addition of 0.1 to 20% is preferred. Use of the dermatologic preparation as skin cosmetics is particularly preferred.

When the dermatologic preparations of the present invention serve as a medicinal dermatologic preparation or skin cosmetic, surfactants such as nonionic surfactants, anionic surfactants, cationic surfactants and amphoteric surfactants may be incorporated. Of these, nonionic surfactants such as polyoxyethylene alkyl ethers, polyoxyethylene fatty acid esters, sorbitan fatty acid esters, polyoxyethylene sorbitan fatty acid esters, fatty acid monoglycerides and glyceryl ethers are preferred. As its content, 0.01 to 20%, particularly 0.1 to 10% in the whole preparation is preferred.

Although no particular limitation is imposed on the content of the diamide derivative (1) in the hair cosmetic of the present invention, preferred is 0.001 to 5% for shampoo, 0.1 to 20% for rinse, treatment, conditioner or styling agent and 0.01 to 5% for hair liquid or hair tonic.

The hair cosmetic of the present invention may contain surfactants such as anionic surfactants, cationic surfactants, nonionic surfactants and amphoteric surfactants and in addition, components ordinarily employed for hair cosmetics. When the hair cosmetic of the present invention is a shampoo, it may contain, as a main active agent, an anionic surfactant such as an alkyl ether sulfate, alkyl sulfate or olefin sulfonate. As its content, 5 to 30%, particularly 10 to 20%, each based on the whole composition, is preferred.

When the cosmetic of the present invention is a hair rinse, conditioner, hair treatment or hair styling agent, it may contain a cationic surfactant such as mono- or di-(long chain alkyl) tetraammonium salt, a nonionic surfactant such as polyoxyethylene alkyl or alkenyl ether or an oil/fat such as liquid paraffin for imparting the hair with good touch feel. The content of the cationic or nonionic surfactant is preferably 0.1 to 50%, particularly 0.5 to 20% in the whole composition.

When the hair cosmetic is a hair liquid or hair tonic, it may contain a nonionic surfactant such as polyoxyethylene.

The nonionic surfactant is preferably added in an amount of 0.01 to 20%, particularly 0.1 to 5% in the whole composition.

The skin cosmetic or hair cosmetic of the present invention containing the diamide derivative (1) may be formulated into an aqueous solution, ethanol solution, emulsion, suspension, gel, solid, aerosol or powder without any limitation.

EXAMPLES

Preparation Example 1

Preparation of Compound (A)

In a flask equipped with a stirrer, a nitrogen inlet tube and a distilling tube, 150 g of dimethyl 8,13-dimethyl-eicosanedioate ("IPS-22M", product of Okamura Seiyu), 159 g of diglycolamine and 7.5 g of sodium methoxide were charged. The mixture was stirred for 5 hours at 140° C. under reduced pressure (20 torr), while distilling off the methanol by-produced. After completion of the reaction, excess diglycolamine was distilled off under reduced pressure. The residue was then washed with water, whereby 200 g (yield: 98%) of the title compound was obtained. The resulting compound 1 (A) has following physical properties:

Colorless Paste $^1$H-NMR (CDCl$_3$, δ): 0.67-0.91(m, 6H), 0.93-1.58(m, 26H), 1.59-1.76(m, 4H), 2.17(t, J=7.2 Hz, 4H), 2.72-3.12(m, 2H), 3.33-3.52(m, 4H), 3.52-3.64(m, 8H), 3.65-3.85(m, 4H), 6.13-6.56(m, 2H).

Preparation Examples 2 to 15

In a similar manner to Example 1 except for the use of the dicarboxylic acid (4) or reactive derivative thereof and, as the amine (5), the compound shown in Table 1 or 2, Compounds (B) to (O) were obtained. These raw materials are shown in Tables 1 and 2, together with the physical properties of the diamide derivatives.

TABLE 1

| | Diamide derivative (1) prepared | Dicarboxylic acid (4) or reactive derivative thereof | Amine (5) | Physical properties |
|---|---|---|---|---|
| Prep. Ex. 2 | Compound (B) | Dimethyl 7,12-dimethyl-7,11-octadecadiene-1,18-dicarboxylate ("IPU-22MM", product of Okamura Seiyu) | Diglycolamine | Colorless paste $^1$H-NMR(CDCl$_3$, δ): 1.05-1.45(m, 16H), 1.45-1.72 (m, 8H), 1.79-2.08(m, 6H), 2.14 (t, J=7.8Hz, 4H), 2.83-3.15 (m, 2H), 3.32-3.47 (m, 4H), 3.47-3.61(m, 8H), 3.61-3.78(m, 4H), 4.52-5.19(m, 2H), 6.26-6.58(m, 2H). |
| Prep. Ex. 3 | Compound (C) | Dimethyleicosanedioate ("SL-20MM", product of Okamura Seiyu) | Diglycolamine | White crystals, Melting point: 135° C. $^1$H-NMR(MeOH-d$_4$, δ): 1.18-1.44(m, 28H), 1.48-1.71 (m, 4H), 2.18(t, J=7.4Hz, 4H), 3.31-3.43 (m, 4H), 3.46-3.60(m, 8H), 3.60-3.71(m, 4H), 4.49-4.68(m, 2H). |
| Prep. Ex. 4 | Compound (D) | Dimethyl sebacate | Diglycolamine | White solid, Melting point: 107° C. $^1$H-NMR(CDCl$_3$, δ): 1.22-1.40(m, 8H), 1.54-1.72 (m, 4H), 2.19(t, J=7.2Hz, 4H), 2.70-2.90 (m, 2H), 3.36-3.54 (m, 4H), 3.54-3.70(m, 8H), 3.70-3.89(m, 4H), 6.13-6.30(m, 2H). |
| Prep. Ex. 5 | Compound (E) | Dimethyl succinate | Diglycolamine | White crystals, Melting point: 85° C. $^1$H-NMR(CDCl$_3$, δ): 2.52(s, 4H), 3.30-3.50 (m, 4H), 3.50-3.64(m, 8H), 3.64-3.88(m, 4H), 7.12-7.33(m, 2H). |
| Prep. Ex. 6 | Compound (F) | Dimethyl 8,13-dimethyleicosanedioate ("IPS-22MM", product of Okamura Seiyu) | 3-Methoxy-propylamine | Colorless paste $^1$H-NMR(CDCl$_3$, δ): 0.67-0.95(m, 6H), 1.00-1.48 (m, 26H), 1.48-1.70(m, 4H), 1.70-1.88(m, 4H), 2.14(t, J=7.2Hz, 4H), 3.23-3.41(m, 10H), 3.41-3.58 (m, 4H), 5.96-6.20(m, 2H). |
| Prep. Ex. 7 | Compound (G) | Dimethyl 8,13-dimethyleicosanedioate ("IPS-22MM", product of Okamura Seiyu) | 3-Dodecyloxy-propylamine | White crystals, Melting point: 36° C. $^1$H-NMR(CDCl$_3$, δ): 0.64-0.98(m, 12H), 0.98-1.46 (m, 62H), 1.46-1.70(m, 8H), 1.70-1.88 (m, 4H), 2.14(t, J=7.2Hz, 4H), 3.26-3.47(m, 8H), 3.47-3.61(m, 4H), 6.09-6.34(m, 2H). |
| Prep. Ex. 8 | Compound (H) | Dimethyl 8,13-dimethyleicosanedioate ("IPS-22MM", product of Okamura Seiyu) | 2-(2-Methoxy-ethoxy)-ethylamine | Colorless paste $^1$H-NMR(CDCl$_3$, δ): 0.69-0.88(m, 6H), 0.93-1.41 (m, 26H), 1.49-1.68(m, 4H), 2.27(t, J=7.2Hz, 4H), 3.36(s, 6H), 3.40-3.68 (m, 16H), 5.88-6.06(m, 2H). |

TABLE 2

| | Diamide derivative (1) prepared | Dicarboxylic acid (4) or reactive derivative thereof | Amine (5) | Physical properties |
|---|---|---|---|---|
| Prep. Ex. 9 | Compound (I) | Dimethyl pentadecanedioate | Diglycolamine | White crystals, Melting point: 127° C. $^1$H-NMR(MeOH-d$_4$, δ): 1.20-1.45(m, 18H), 1.45-1.75 (m, 4H), 2.18(t, J=7.4Hz, 4H), 3.25-3.45 |

TABLE 2-continued

| Diamide derivative (1) prepared | Dicarboxylic acid (4) or reactive derivative thereof | Amine (5) | Physical properties |
|---|---|---|---|
| | | | (m, 8H), 3.52(t, J=5H.1Hz, 4H), 3.60-3.75(m, 4H), 4.60-4.70(m, 2H). |
| Prep. Ex. 10 | Compound (J) | Dimethyl brassylate | Diglycolamine | White crystals, Melting point: 120° C. $^1$H-NMR(MeOH-d$_4$, δ): 1.20-1.45(m, 14H), 1.50-1.70 (m, 4H), 2.18(t, J=7.4Hz, 4H), 3.25-3.45 (m, 8H), 3.52(t, J=5.0Hz, 4H), 3.60-3.75(m, 4H), 4.60-4.70(m, 2H). |
| Prep. Ex. 11 | Compound (K) | Dimethyl dodecanedioate | Diglycolamine | White solid, Melting point: 118° C. $^1$H-NMR(MeOH-d$_4$, δ): 1.20-1.45(m, 12H), 1.45-1.75 (m, 4H), 2.18(t, J=7.4 Hz, 4H), 3.25-3.45 (m, 8H), 3.52(t, J=5.1Hz, 4H), 3.60-3.75(m, 4H), 4.60-4.70(m, 2H). |
| Prep. Ex. 12 | Compound (L) | Dimethyl Eicosanedioate | 3-Methoxy-propylamine | White crystals, Melting point: 134° C. $^1$H-NMR(CDCl$_3$, δ): 1.15-1.40(m, 32H), 1.52-1.70 (m, 4H), 1.77(quintet, J=6.1Hz, 4H), 2.15 (t, J=7.6Hz, 4H), 3.30-3.43(m, 4H), 3.35(s, 6H), 3.48(t, J=5.7Hz, 4H), 5.90-6.10(m, 2H). |
| Prep. Ex. 13 | Compound (M) | Dimethyl dodecanedioate | 3-Methoxy-propylamine | White crystals, Melting point: 129° C. $^1$H-NMR(CDCl$_3$, δ): 1.15-1.40(m, 12H), 1.50-1.70 (m, 4H), 1.70-1.90(m, 4H), 2.15 (t, J=6.1Hz, 4H), 3.30-3.45(m, 4H), 3.35(s, 6H), 3.48(t, J=5.8Hz, 4H), 5.95-6.05(m, 2H). |
| Prep. Ex. 14 | Compound (N) | Dimethyl sebacate | 3-Methoxy-propylamine | White crystals, Melting point: 125° C. $^1$H-NMR(CDCl$_3$, δ): 1.20-1.45(m, 8H), 1.50-1.70 (m, 4H), 1.71-1.90(m, 4H), 2.15(t, J=7.5Hz, 4H), 3.25-3.45(m, 4H), 3.35(s, 6H), 3.48 (t, J=5.8Hz, 4H), 6.00-6.20(m, 2H). |
| Prep. Ex. 15 | Compound (O) | Dimethyl sebacate | 3-Dodecyloxy-propylamine | White crystals, Melting point: 134° C. $^1$H-NMR(CDCl$_3$, δ): 0.80-1.00(m, 6H), 1.15-1.45 (m, 44H), 1.45-1.70(m, 8H), 1.76(quintet, J=6.1Hz, 4H), 2.13(t, J=7.6Hz, 4H), 3.30-3.48 (m, 8H) 3.52(t, J=5.7Hz, 4H), 6.05-6.25(m, 2H) |

Preparation Example 16

In a flask equipped with a stirrer, a nitrogen inlet tube and a distilling tube, 537 g of 8,13-dimethyl-eicosanedioic acid ("IPS-22", product of Okamura Seiyu) was charged, followed by dropwise addition of 381 g of diglycolamine over 4 hours under stirring at 180° C. in a nitrogen gas stream. After saturation for 4 hours under the same conditions, saturation was conducted for further 4 hours at 200° C. The above-described dropwise addition and saturation were conducted in a nitrogen gas stream while distilling off water by-produced. After completion of the reaction, excess diglycolamine was removed by distillation under reduced pressure and steaming. In a molecular distillation apparatus, a low-boiling-point substance was removed under the conditions of 200° C. and 0.7 Pa, whereby 680 g (yield: 86%) of the crude Compound (A) was obtained as a pale yellow paste. Mainly for bleaching, 20 g of the compound was dissolved in 20.0 g of ethanol and 0.40 g of activated charcoal was added to the resulting solution, followed by stirring at 80° C. for 2 hours. The activated charcoal was filtered out and the residue was concentrated under reduced pressure, whereby 19.9 g of Compound (A) was obtained as a colorless paste.

Preparation Example 17

In a flask equipped with a stirrer, a nitrogen inlet tube and a distilling tube, 770 g of sebacic acid was charged, followed by dropwise addition of 1001 g of diglycolamine over 4 hours under stirring at 200° C. in a nitrogen gas stream. The reaction mixture was saturated for 5 hours under the same conditions. The above-described dropwise addition and saturation were conducted in a nitrogen gas stream while distilling off water by-produced. After completion of the reaction, excess diglycolamine was removed by distillation under reduced pressure and steaming, whereby 1410 g (yield: 98%) of the crude Compound (D) was obtained as white crystals. The crystals were re-crystallized from 4510 g of a 6.25% aqueous solution of sodium sulfate, whereby 1085 g (yield: 76%) of Compound (D) was obtained as white crystals.

Preparation Example 18

In a flask equipped with a stirrer, a nitrogen inlet tube and a distilling tube, 100 g of 8,13-dimethyl-eicosanedioic acid ("IPS-22", product of Okamura Seiyu) was charged, followed by the dropwise addition of 61 g of 3-methoxypropylamine over 3 hours at 180° C. under stirring in a nitrogen gas stream. After saturation for 3 hours under the same conditions, saturation was conducted for further 5 hours at 200° C. The above-described dropwise addition and saturation were conducted under a nitrogen gas stream while distilling off water by-produced. After completion of the reaction, excess 3-methoxypropylamine was removed by distillation under reduced pressure and steaming, whereby 137 g (yield: 99%) of the crude Compound (F) was obtained as a pale yellow paste. The crude Compound (F) was distilled (at 220° C. and 0.7 to 0.3 Pa), whereby 106 g (yield: 77%) of Compound (F) was obtained as a colorless paste.

Test 1

Dermatologic preparations (invention products) composed of 33% of each of the diamide derivatives prepared in Preparation Examples 1 to 18 and 67% of vaseline were prepared. Their effects on skin conductance and chapping were evaluated in the below-described manner. For comparison, a dermatologic preparation (Comparative Product 1) composed of vaseline alone was evaluated in the same manner. Table 3 shows the results.

(Test Method)

Ten female subjects aged 20 to 50 years, who suffered chapping in cheeks in winter, were employed. Different dermatologic preparations were applied on the right and left cheeks of the subjects for 2 weeks, respectively. On the next day after completion of the application for 2 weeks, the following items were examined.

(1) Skin Conductance

The face of each subject was washed with warm water of 37° C. After she was allowed to stand in a room at 20° C. under a humidity of 45% for 20 minutes, the water content of the horny layer was measured using a skin conductance meter (product of IBS Co., Ltd.).

(2) Skin Chapping Score

Skin chapping was observed with naked eyes and evaluated based on the following criteria. Each score is expressed in the mean value.

0: No chapping is observed.
1: Slight chapping is observed.
2: Chapping is observed.
3: Somewhat serious chapping is observed.
4: Serious chapping is observed.

TABLE 3

| Dermatologic preparation | Diamide derivative | Skin conductance | Skin chapping score |
| --- | --- | --- | --- |
| Invention product 1 | Compound (A) | 28 | 0.6 |
| Invention product 2 | Compound (B) | 25 | 0.9 |
| Invention product 3 | Compound (C) | 21 | 1.0 |
| Invention product 4 | Compound (D) | 30 | 0.5 |
| Invention product 5 | Compound (E) | 18 | 1.0 |
| Invention product 6 | Compound (F) | 20 | 1.2 |
| Invention product 7 | Compound (G) | 17 | 1.1 |
| Invention product 8 | Compound (H) | 19 | 1.3 |
| Invention product 9 | Compound (J) | 23 | 0.8 |
| Invention product 10 | Compound (L) | 19 | 1.3 |
| Invention product 11 | Compound (N) | 18 | 1.5 |
| Comparative product 1 (vaseline alone) | — | 5 | 2.7 |

The results show that the invention products 1 to 11 were superior to the comparative product in effects of increasing the water content of the horny layer and remedying skin chapping.

Test 2

Dermatologic preparations (invention products) of the present invention composed of 10% of each of the diamide derivatives prepared in Preparation Examples 1 to 18 and 90% of squalane were prepared and their transepidermal water loss and percutaneous absorption were evaluated by the below-described test method. For comparison, a dermatologic preparation (Comparative Product 2) composed of squalane alone was also evaluated by the test. Table 4 shows the results.

(Test Method)

Wistar male rats were fed with a feed free from essential fatty acids and the resulting rats with essential fatty acid deficiency were employed in this test. The dorsal part of the rat showing essential fatty acid deficiency was carefully shaven and each dermatologic preparation to be evaluated was applied thereto once a day for 2 weeks. A group consisting of 5 rats was provided for the test of each dermatologic preparation. After 2 weeks, the following items were examined.

(1) Transepidermal Water Loss

The dorsal part of the test rat was washed with warm water and the animal was the allowed to stand in a room (at 23° C. under a humidity of 45%) for 1 hour. The transepidermal water loss was then measured with an evaporimeter. Each measured value is expressed in mean value.

(2) Percutaneous Water Absorption

After the dorsal skin of the rat was washed with warm water of 37° C., it was cut and fixed in a percutaneous absorption chamber with the epidermal side thereof directed upward. A lower receiver of the chamber was filled with a phosphate buffer solution while a container on the epidermal side thereof was charged with 1 ml of a phosphate buffer solution containing 37 KBq of $^{14}$C-salicylic acid. Two hours after they were allowed to stand, 1 mL of the phosphate buffer solution was taken out of the lower receiver and the radioactivity of the $^{14}$C-salicylic acid which had penetrated into it was measured. Each value is expressed in mean value.

TABLE 4

| Dermatologic preparation | Diamide derivative | Transepidermal water loss | Percutaneous absorption |
| --- | --- | --- | --- |
| Invention product 12 | Compound (A) | 12 | 572 |
| Invention product 13 | Compound (B) | 12 | 558 |
| Invention product 14 | Compound (C) | 21 | 1685 |
| Invention product 15 | Compound (D) | 15 | 997 |
| Invention product 16 | Compound (E) | 25 | 1772 |
| Invention product 17 | Compound (F) | 20 | 1487 |
| Invention product 18 | Compound (G) | 16 | 1096 |
| Invention product 19 | Compound (H) | 23 | 2036 |
| Invention product 20 | Compound (I) | 18 | 1197 |
| Invention product 21 | Compound (J) | 21 | 1490 |
| Invention product 22 | Compound (K) | 22 | 1694 |
| Invention Product 23 | Compound (L) | 15 | 705 |
| Invention Product 24 | Compound (M) | 25 | 2038 |
| Invention Product 25 | Compound (N) | 23 | 1560 |
| Invention Product 26 | Compound (O) | 27 | 2476 |
| Comparative product 2 (squalane alone) | — | 31 | 2994 |

The results show that the invention products 12 to 26 were superior to the comparative product 2 in effects of suppressing transepidermal water loss and percutaneous absorption and remedying chapping.

Test 3

Hair rinses having the compositions as listed in Table 5 were prepared and excessive dryness and touch feel of the hair after treated with the resulting hair rinses were evaluated by a panel of 5 experts in accordance with the below-described criteria. The results are shown in Table 6.

(Evaluation Criteria)

−2: Bad
−1: slightly bad
0: neither good nor bad
+1: Slightly good
+2: Good

TABLE 5

| Composition (%) | Invention product 27 | Invention Product 28 | Invention Product 29 | Comparative Product 3 |
|---|---|---|---|---|
| Distearyl dimethyl ammonium chloride | 2 | 2 | 2 | 2 |
| Propylene glycol | 3 | 3 | 3 | 3 |
| Compound (A) | 1 | — | — | — |
| Compound (D) | — | 1 | — | — |
| Compound (F) | — | — | 1 | — |
| Water | Balance | Balance | Balance | Balance |

TABLE 6

| Evaluation items | Invention product 27 | Invention product 28 | Invention product 29 | Comparative Product 3 |
|---|---|---|---|---|
| Excessive dryness of the hair | +1.4 | +1.2 | +1.6 | −0.4 |
| Favorable touch feel | +1.2 | +1.6 | +1.8 | −0.5 |

Apparent from the above-described table, the invention products 27 to 29 are superior to the comparative product 3 in the effects of alleviating excessive hair dryness and improving the touch feel of the hair.

Example 1

A skin lotion having the composition as shown in Table 7 was prepared in a conventional manner. The resulting hair lotion exhibited excellent effects of preventing or remedying chapping. Compound (A) and Compound (F) were excellent in miscibility and mixing stability.

TABLE 7

| (Composition) | (%) |
|---|---|
| Compound (A) or Compound (F) | 1 |
| Glycerin monostearate | 1 |
| Ethanol | 15 |
| Propylene glycol | 4 |
| Isopropyl palmitate | 3 |
| Lanolin | 1 |
| Methyl paraoxybenzoate | 0.1 |
| Ceramide | 1 |
| Perfume | Trace |
| Colorant | Trace |
| Water | Balance |

Example 2

An O/W cream having the composition as shown in Table 8 was prepared in a conventional manner. The resulting O/W cream exhibited excellent effects of preventing or remedying chapping. Compound (D) and Compound (F) were excellent in miscibility and mixing stability.

TABLE 8

| (Composition) | (%) |
|---|---|
| Compound (D) or Compound (F) | 3.5 |
| Squalane | 2.0 |
| Neopentyl glycol dicaprate | 3.0 |
| Polyoxyethylene (20) sorbitan monostearate | 2.1 |
| Sorbitan monostearate | 0.9 |
| Polyoxyethylene hardened castor oil ("EMANON CH-40", product of Kao Corp.) | 1.0 |

TABLE 8-continued

| (Composition) | (%) |
|---|---|
| Monoisostearyl glyceryl ether | 0.2 |
| 86% glycerin | 5.0 |
| Methyl paraben | 0.3 |
| Water | Balance |

Example 3

A shampoo having the composition as shown in Table 9 was prepared in a conventional manner. This shampoo improved the touch feel of the hair and prevented remedied the chapping of the scalp. Compound (F) and Compound (A) were excellent in miscibility and mixing stability.

TABLE 9

| (Composition) | (%) |
|---|---|
| Polyoxyethylene (25) lauryl ether sulfate Sodium salt | 15 |
| Coconut oil fatty acid diethanol amide | 3 |
| Compound (A) or Compound (F) | 2 |
| Perfume | 0.5 |
| Colorant | Trace |
| Citric acid | Trace |
| Water | Balance |

Example 4

A hair liquid composition having the composition as shown in Table 10 was prepared in a conventional manner. The resulting hair liquid composition imparted the hair with excellent style retention and manageability and good touch feel. Compound (D) and Compound (F) were excellent in miscibility and mixing stability.

TABLE 10

| (Composition) | (%) |
|---|---|
| Compound (D) or Compound (F) | 1 |
| Polyoxypropylene (30) butyl ether | 15.0 |
| Ethanol | 40.0 |
| Water | Balance |
| Perfume | 0.3 |

INDUSTRIAL APPLICABILITY

Diamide derivatives (I) penetrate the lipid layer between horny cells, thereby exerting effects of improving (maintaining•reinforcing) water retention capacity and barrier functions of the horny layer; and by these effects, they prevent or remedy the skin chapping and prevent aging of the skin. When they are applied to the hair, they penetrate into the hair, thereby heightening their protective effects, improving the touch feel of the hair and preventing or remedying the chapping of the scalp. In addition, they have good solubility and stability in a base and have excellent mixing stability, making it possible to prepare a dermatological preparation efficiently at a low cost.

The invention claimed is:

1. A dermatologic preparation, which comprises a diamide derivative represented by the following formula (1):

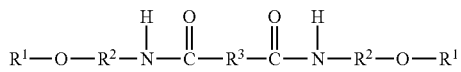

(wherein, $R^1$ represents a linear or branched hydrocarbon group having 1 to 22 carbon atoms which may be substituted by one or more hydroxy and/or alkoxy groups, $R^2$ represents a linear or branched divalent hydrocarbon group having 1 to 12 carbon atoms, and $R^3$ represents a linear or branched divalent hydrocarbon group having 1 to 42 carbon atoms).

2. A dermatologic preparation according to claim 1, which is a cosmetic preparation.

3. A dermatologic preparation as claimed in claim 1 or 2, wherein $R^1$ represents a linear or branched alkyl group having 1 to 22 carbon atoms which may have 1 to 3 substituents selected from a hydroxy group and $C_{1-6}$ alkoxy groups, $R^2$ represents a linear or branched hydrocarbon group having 1 to 12 carbon atoms, and $R^3$ represents an alkylene group or an alkenylene group having 1 to 4 double bonds, which alkylene or alkenylene group may be linear or branched and has 2 to 34 carbon atoms.

4. A humectant comprising, as an effective ingredient, a diamide derivative represented by the following formula (1):

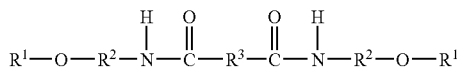

(wherein, $R^1$ represents a linear or branched hydrocarbon group having 1 to 22 carbon atoms which may be substituted by one or more hydroxy and/or alkoxy groups, $R^2$ represents a linear or branched divalent hydrocarbon group having 1 to 12 carbon atoms, and $R^3$ represents a linear or branched divalent hydrocarbon group having 1 to 42 carbon atoms).

5. A skin barrier function reinforcing agent comprising, as an effective ingredient, a diamide derivative represented by the following formula (1):

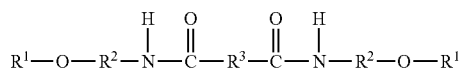

(wherein, $R^1$ represents a linear or branched hydrocarbon group having 1 to 22 carbon atoms which may be substituted by one or more hydroxy and/or alkoxy groups, $R^2$ represents a linear or branched divalent hydrocarbon group having 1 to 12 carbon atoms, and $R^3$ represents a linear or branched divalent hydrocarbon group having 1 to 42 carbon atoms).

6. The dermatologic preparation of claim 1, where $R^1$ represents a linear hydrocarbon having 1 carbon atom, $R^2$ represents a linear divalent hydrocarbon having 3 carbon atoms and $R^3$ represents a branched divalent hydrocarbon having 20 carbon atoms.

7. The humectant of claim 4, wherein where $R^1$ represents a linear hydrocarbon having 1 carbon atom, $R^2$ represents a linear divalent hydrocarbon having 3 carbon atoms and $R^3$ represents a branched divalent hydrocarbon having 20 carbon atoms.

8. The skin barrier function reinforcing agent of claim 5, wherein where $R^1$ represents a linear hydrocarbon having 1 carbon atom, $R^2$ represents a linear divalent hydrocarbon having 3 carbon atoms and $R^3$ represents a branched divalent hydrocarbon having 20 carbon atoms.

* * * * *